United States Patent
Kirmse

(10) Patent No.: US 12,268,908 B2
(45) Date of Patent: Apr. 8, 2025

(54) COOLING ELEMENT SYSTEM FOR USE WITHIN A COOLING DEVICE OF A CLOSED-CIRCUIT RESPIRATOR

(71) Applicant: Dräger Safety AG & Co. KGaA, Lübeck (DE)

(72) Inventor: Sören Kirmse, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 864 days.

(21) Appl. No.: 17/076,148

(22) Filed: Oct. 21, 2020

(65) Prior Publication Data
US 2021/0121717 A1  Apr. 29, 2021

(30) Foreign Application Priority Data
Oct. 24, 2019 (DE) .................... 10 2019 007 409.2

(51) Int. Cl.
*A62B 9/00* (2006.01)
*A61M 16/00* (2006.01)

(52) U.S. Cl.
CPC ......... *A62B 9/003* (2013.01); *A61M 16/0093* (2014.02)

(58) Field of Classification Search
CPC ............ A62B 9/003; F28D 2020/0008; F24F 5/0017; F24F 5/0021
See application file for complete search history.

(56) References Cited

U.S. PATENT DOCUMENTS

| | | | | |
|---|---|---|---|---|
| 2,877,000 A | * | 3/1959 | Person | F28F 9/22 165/130 |
| 2,942,855 A | * | 6/1960 | Wellensiek | F28D 7/10 165/135 |
| 4,611,589 A | | 9/1986 | Pasternack | |
| 4,612,974 A | * | 9/1986 | Yanadori | F28D 20/02 126/400 |
| 4,784,218 A | * | 11/1988 | Holl | F28F 13/02 165/DIG. 405 |
| 4,793,402 A | * | 12/1988 | Yano | C09K 5/063 126/400 |

(Continued)

FOREIGN PATENT DOCUMENTS

| | | | |
|---|---|---|---|
| CN | 110025900 A | * | 7/2019 |
| DE | 1604194 A1 | * | 8/1970 |

(Continued)

*Primary Examiner* — Kathryn E Ditmer
(74) *Attorney, Agent, or Firm* — McGlew and Tuttle, P.C.

(57) ABSTRACT

A cooling element system (100), for use within a cooling device (590) of a closed-circuit respirator (691), includes a plurality of cooling elements and a collar (120). The cooling elements each have an element housing (112), having a liquid-tight closure (114), filled or fillable with a coolant. The element housings allow for a common mounting arrangement of the number of cooling elements within the cooling device. The collar encloses the cooling elements in the common mounting arrangement and has a carrying area (122), which is configured to carry the number of cooling elements in the common mounting arrangement at the carrying area. A removal of the number of cooling elements, in the common mounting arrangement, from the cooling device and an insertion into the cooling device, are possible by means of the carrying area.

20 Claims, 6 Drawing Sheets

(56) References Cited

U.S. PATENT DOCUMENTS

| | | | | |
|---|---|---|---|---|
| 4,924,935 A * | 5/1990 | Van Winckel | ........ | F28D 20/02 |
| | | | | 165/104.11 |
| 5,157,941 A * | 10/1992 | Cur | ........ | F25B 39/02 |
| | | | | 165/146 |
| 5,421,172 A * | 6/1995 | Jones | ........ | F25D 3/08 |
| | | | | 62/530 |
| 5,644,929 A * | 7/1997 | Tanaka | ........ | B60H 1/323 |
| | | | | 62/434 |
| 5,662,161 A * | 9/1997 | Hughes | ........ | A62B 9/003 |
| | | | | 128/201.13 |
| 5,784,897 A * | 7/1998 | Shin | ........ | B21C 37/26 |
| | | | | 165/184 |
| 6,067,813 A * | 5/2000 | Smith | ........ | A45C 11/20 |
| | | | | 62/530 |
| 6,094,933 A * | 8/2000 | Forsthuber | ........ | F25D 3/005 |
| | | | | 62/434 |
| 7,357,247 B2 * | 4/2008 | Guenther | ........ | B65D 71/50 |
| | | | | 206/139 |
| 2010/0126199 A1 * | 5/2010 | Trieu | ........ | F24F 5/0017 |
| | | | | 62/291 |
| 2011/0179807 A1 * | 7/2011 | Holloway | ........ | F24F 5/0017 |
| | | | | 62/530 |
| 2013/0235518 A1 * | 9/2013 | Kuo | ........ | F24F 5/0017 |
| | | | | 361/679.32 |
| 2015/0211804 A1 * | 7/2015 | Kuo | ........ | F28D 17/02 |
| | | | | 165/10 |
| 2015/0211805 A1 * | 7/2015 | Kuo | ........ | F28D 20/00 |
| | | | | 165/104.34 |
| 2016/0039269 A1 * | 2/2016 | Kumar | ........ | B60H 1/00407 |
| | | | | 62/77 |
| 2019/0093909 A1 * | 3/2019 | Floyd | ........ | A45C 11/20 |
| 2022/0217875 A1 * | 7/2022 | Sawafta | ........ | H05K 7/2079 |

FOREIGN PATENT DOCUMENTS

| | | | |
|---|---|---|---|
| DE | 3345584 C1 | | 6/1985 |
| DE | 102013221770 A1 | | 4/2015 |
| EP | 0610823 A1 | * | 8/1994 |
| FR | 1425721 A | * | 1/1966 |
| FR | 2490800 A1 | | 3/1982 |
| FR | 2658596 A1 | * | 8/1991 |
| JP | 59049436 A | * | 3/1984 |
| JP | 2006027031 A | * | 2/2006 |
| WO | WO-2015051895 A1 | * | 4/2015 |
| WO | WO-2017216148 A1 | * | 12/2017 |
| WO | 2019202215 A1 | | 10/2019 |

* cited by examiner

COOLING ELEMENT SYSTEM FOR USE WITHIN A COOLING DEVICE OF A CLOSED-CIRCUIT RESPIRATOR

CROSS REFERENCE TO RELATED APPLICATIONS

This application claims the benefit of priority under 35 U.S.C. § 119 of German Application 10 2019 007 409.2, filed Oct. 24, 2019, the entire contents of which are incorporated herein by reference.

TECHNICAL FIELD

The present invention pertains to a cooling element system for use within a cooling device of a closed-circuit respirator. The present invention pertains, furthermore, to a cooling device for the closed-circuit respirator and to a closed-circuit respirator with a cooling device.

TECHNICAL BACKGROUND

The use of a cooling device in a closed-circuit respirator for cooling a breathing gas flow is known and necessary. A lime typically used as absorber for treating the gas, which treats the gas by removing $CO_2$, thus produces heat continuously. In the closed breathing gas circuit, this causes during the use of the closed-circuit respirator the temperature of the inhaled gas to rise for the user of the closed-circuit respirator into a temperature range that is at least extremely uncomfortable for the user during the inhalation. Provisions are therefore made for a continuous cooling of the breathing gas circuit by a cooling device. The cooling device has a coolant, which is typically cooled to below its melting point prior to the use of the closed-circuit respirator.

The coolant is preferably ice or a coolant formed as a coolant configured as a phase-change material (PCM), which is used in the closed-circuit respirator within the cooling element, e.g., within a liquid accumulator. It is especially advantageous in a PCM coolant that it stores a large part of the thermal energy fed into it in the form of latent heat for a phase change from solid to liquid. As a result, very large quantities of thermal energy can be stored in a narrow temperature range around the melting point. A PCM coolant can make possible as a result a constant temperature level for the breathing air within the breathing gas stream of the closed-circuit respirator.

SUMMARY

An object of the present invention is to make possible an especially simple handling of a number of cooling elements, especially an especially robust application of the number of cooling elements.

A cooling element system for use within a cooling device of a closed-circuit respirator with a number of cooling elements and with a collar is proposed according to the present invention to accomplish this object.

The number of cooling elements have an element housing each, which has a fluid-tight closure and is filled or can be filled with a coolant. The element housings of the number of cooling elements make possible a common mounting arrangement of the number of cooling elements within the cooling device.

The collar is configured to enclose, especially to detachably enclose, the number of cooling elements in the presence of the common mounting arrangement, especially to be in contact with cooling elements from the number of cooling elements, and it has a carrying area, which is configured to carry the number of cooling elements at the carrying area in the presence of the common mounting arrangement. As a result, removal of the number of cooling elements in the presence of the common mounting arrangement from the cooling device and insertion into the cooling device via the carrying area are possible.

It was found within the framework of the present invention that the removal of the number of cooling elements from the cooling device may represent a problem, because a particular cooling element may have changed its volume or its position, as a result of which it is possibly stuck within the cooling device, so that a manual removal by simply grasping is not possible. Furthermore, it was found that in case of a plurality of cooling elements the effort involved in the removal of these cooling elements can be reduced by the fact that the number of cooling elements can be removed together by means of a collar that is in contact with these cooling elements.

The provision of a carrying area at the collar advantageously makes possible an especially comfortable removal and insertion of the number of cooling elements. The carrying area is characterized in that it is suitable for a manual grasping of the collar at the carrying area.

In case of a change in the volume of a coolant within a cooling element and/or in case a cooling element is frozen solid at the surrounding housing of the cooling device, a strong pulling force can be transmitted to the number of cooling elements, so that the cooling elements can be reliably removed or changed even if the correspondingly equipped closed-circuit respirator is used under adverse conditions.

Further, the collar with the carrying area is preferably configured such that carrying of the number of cooling elements via the carrying area is possible over the long run. As a result, the number of cooling elements can be transported especially comfortably.

The cooling element system according to the present invention makes especially advantageously possible a rapid replacement and/or a rapid insertion of the number of cooling elements into the cooling device. This is especially advantageous in case of the use of the correspondingly equipped closed-circuit respirator within the framework of applications that are critical in terms of time, for example, firefighting.

The common mounting arrangement is a predefined arrangement of the cooling elements from the number of cooling elements relative to one another. An especially compact arrangement of the cooling elements within the cooling device can be achieved due to the provision of a common mounting arrangement for inserting the number of cooling elements into the cooling device. As a result, an especially large quantity of coolant can cool a breathing gas stream of the closed-circuit respirator within the cooling device.

The collar may enclose the number of cooling elements permanently or detachably. The collar is preferably fastened detachably to the number of cooling elements. The collar is especially preferably fastened detachably to the number of cooling elements by a non-positive and/or positive-locking connection.

The carrying area may be configured according to the present invention as a grasping area, which supports carrying of the cooling element system, but an additional area of the cooling element also has to be touched in order to make secure carrying of the entire cooling element system possible. The carrying area may be configured as a non-contiguous carrying area, so that at least two areas of the collar must be grasped in order to carry the cooling element system according to the present invention. However, it is especially preferably possible to carry the entire cooling element system by a single, contiguous carrying area configured as a grip, band, projection or the like.

The liquid-tight closure may be a detachable closure, e.g., a screw cap, or a permanent closure, especially a permanent, non-detachable closure closed, for example, by welding during the manufacture of the cooling element.

Preferred embodiments of the cooling element system according to the present invention will be described below.

The collar is formed from a plastic, especially from an elastomer in an especially preferred embodiment. The collar can be manufactured in an especially simple and cost-effective manner in this embodiment. The use of an elastomer makes it, furthermore, possible to use the collar, which encloses the number of cooling elements according to the present invention, to cushion a contact between the cooling element and the cooling device. As a result, the collar can act especially advantageously as an impact protection for the cooling elements from the number of cooling elements. This supports the durability of the cooling element system according to the present invention. In particular, wear of the element housing is reduced at possible impact points in the area of an impact on the cooling device. Furthermore, this leads to a reduction of the generation of noise within a corresponding closed-circuit respirator equipped with the cooling element system.

In another, especially preferred embodiment, the number of cooling elements comprise at least two cooling elements. The use of the collar according to the present invention is especially advantageous in this embodiment, because a separate removal and insertion of the plurality of cooling elements through the common collar is avoided. In a variant of this embodiment, the cooling element system comprises at least four, especially at least six cooling elements. The use of such a plurality of cooling elements leads to an enlargement of an entire outer surface of all element housings. As a result, the contact area between breathing the gas stream and the cooling element system can be enlarged, as a result of which the efficiency of the cooling element system can be improved.

The element housings of the number of cooling elements have a plate-like (plate shape) configuration in another advantageous embodiment. Such a plate shape structure can be stacked readily and can therefore lead to cooling elements that can be arranged in an especially compact manner and hence to an especially compact common mounting arrangement. Furthermore, a plate shape structure of the cooling elements makes possible an especially large outer surface of the cooling elements relative to the volume of a cooling element, which volume is enclosed by the element housing. The plate shape element housing according to this embodiment therefore makes possible an especially efficient cooling of the breathing gas stream of the closed-circuit respirator. In addition, due to its good stackability, the plate shape structure of the cooling elements makes possible a space-saving arrangement of a plurality of cooling elements in a cooling device, e.g., in a refrigerator, in order to cool the cooling elements prior to a use of the closed-circuit respirator.

In an especially preferred variant of the above embodiment, the common mounting arrangement of the number of cooling elements comprises a layering of the plate shape element housings to a stack of plates. Such a common mounting arrangement permits an especially compact arrangement of the plate shape element housings. As a result, an especially large amount of coolant can be arranged within the cooling device as a filling of a particular cooling element. Furthermore, such a stack of plates can be held together reliably by the collar enclosing this stack of plates and the stack of plates can be removed and inserted via the carrying area.

In an especially advantageous example of the above variant, the element housings having a plate shape configuration have each at least one elevation and a corresponding depression, so that a respective elevation of an element housing meshes within the stack of plates with a respective depression of another element housing of the stack of plates. The provision of elevation and depression in this example leads to an especially stable stack of plates. In particular, a displacement of a single plate within the stack of plates is prevented, because an individual plate is held in its position by the meshing of an elevation and of a depression. Each element housing of a number of cooling elements preferably has at least one elevation and at least one corresponding depression. Each element housing of the number of cooling elements especially preferably has a plurality of elevations and a plurality of corresponding depressions. As a result, adjacent element housings within the stack of plates preferably mesh mutually with one another and thereby stabilize the stack of plates. The cooling elements within the stack of plates can only be removed from one another in this example by being lifted off from one another. According to the present invention, the collar must only prevent in this variant such a lifting off of cooling elements of the stack of plates in order to make possible a stable carrying and movement of the complete stack of plates.

In an advantageous variant of the above embodiment, the collar is in contact on at least two opposite sides of the stack of plates of the number of cooling elements. Due to the contact according to this variant, stable holding of the stack of plates by the collar is ensured in an especially reliable manner. In a preferred variant of this embodiment, the collar is in contact on at least four sides of the stack of plates, especially on six sides of the stack of plates of the number of cooling elements. The contact of the collar on four to six sides leads to an especially reliable and stable arrangement of the collar at the stack of plates. Due to the contact of the collar on at least four sides, a positive-locking and/or non-positive detachable fastening of the collar at the stack of plates can be made possible. For example, a collar formed from an elastomer can be stretched elastically and led around the stack of plates in order to hold as a result the stack of plates as a common mounting arrangement of the number of cooling elements in a non-positive-manner.

In an especially preferred embodiment of the cooling element system according to the present invention, the element housings of the number of cooling elements are shaped such that a collar depression encloses this common mounting arrangement at least partially in the common mounting arrangement. This collar depression is configured in this embodiment to allow a contact of the collar within the collar depression. The collar depression thus supports a positive-locking, detachable connection between the collar and the number of cooling elements in the common mounting arrangement. In an especially preferred variant of this embodiment, the common mounting arrangement is a stack of plates from element housings having a plate shape configuration. In this case the collar depression preferably runs over at least two opposite sides of the stack of plates, especially over at least two pairs of two respective opposite sides of the stack of plates. The collar depression preferably has a depth of at least half of the collar thickness of the collar in this case. The collar depression especially preferably has a depth that is smaller than the collar thickness of the collar. It is ensured hereby that the collar cushions the cooling element system against shocks acting on the cooling device.

In another advantageous embodiment, the collar has at least one flow guide opening. The collar basically reduces a contact between breathing gas stream of the closed-circuit respirator and the cooling element in the areas in which it is in contact with a cooling element from the number of cooling elements. In addition, it reduces the breathing gas stream at the cooling elements located on the outside within the common mounting arrangement, because it hinders a gas stream along these cooling elements. At least one flow guide opening, which makes the breathing gas stream uniform in the area of the cooling elements located on the outside within the common mounting arrangement and makes a uniform cooling of the breathing gas possible thereby, is therefore provided in this embodiment. Furthermore, the flow guide opening may be configured to enlarge a contact area between the cooling element and the breathing gas stream by the breathing gas stream coming into contact through the flow guide opening with the respective cooling element. The collar preferably has a plurality of flow guide openings.

At least one cooling element of the number of cooling elements is preferably filled with a PCM coolant. In particular, all cooling elements of the number of cooling elements are preferably filled with a PCM coolant.

According to another aspect of the present invention, a cooling device for a closed-circuit respirator with a cooling element system according to at least one of the above embodiments and with a device housing is proposed to accomplish the above-mentioned object.

The device housing has a gas inlet, which is configured to admit a gas to be cooled into the device housing, and it has, furthermore, a gas outlet, which is configured to let the gas admitted into the device housing through the gas inlet out of the device housing. Finally, the device housing according to this additional aspect of the present invention has, furthermore, a device volume, which is enclosed by a housing wall of the device housing and which can replaceably accommodate the cooling element system, the device housing being configured such that a gas stream of the gas to be cooled, namely, the breathing gas stream of the corresponding closed-circuit respirator, can flow from the gas inlet through the cooling element system arranged in the device volume to the gas outlet.

The combination of cooling element system and device housing according to this additional aspect of the present invention makes it advantageously possible for the cooling device to be configured corresponding to the common mounting arrangement of the number of cooling elements. The space within the cooling device is utilized as a result especially efficiently by the number of cooling elements, so that an especially small overall height of the cooling device is possible. Furthermore, an arrangement in which the cooling element system and the cooling device are coordinated with one another makes it possible that the gas stream can pass uniformly through the cooling element system and uniform cooling of the gas will take place as a result. Furthermore, a positioning that is observed especially precisely for an optimal flow of the gas stream through the cooling element system is made possible by the reliable arrangement of the cooling elements in the frame of the predefined common mounting arrangement within the device volume of the cooling device. Since an especially efficient cooling is possible, the quantity of coolant necessary for a sufficient cooling can also be reduced hereby.

In an especially preferred embodiment of the cooling device according to the present invention, the collar is configured to enclose the common mounting arrangement of the number of cooling elements such that a bead of the collar, which bead points away from the number of cooling elements and encloses the common mounting arrangement at least partially and especially completely, is in contact with the housing wall of the device housing in the inserted state of the cooling element system and thereby limits the gas stream of the gas to be cooled. This bead may seal especially an area between the cooling element system and the housing wall and thereby force a gas stream through the cooling element system by a flow of gas around the cooling element system being prevented or greatly reduced. Furthermore, the contact of the bead with the housing wall ensures an especially efficient cushioning of a movement of the cooling element system relative to the device housing of the cooling device. Damage to the cooling element system can be reliably prevented hereby. In an especially preferred variant of this embodiment, at least one flow guide opening, which makes possible a certain air stream of the gas to be cooled around the cooling element system, is provided in the bead.

An advantageous cooling device for a closed-circuit respirator may also be provided by a cooling element system with the collar according to the present invention if no carrying area is provided at the collar contrary to the teaching of the present invention. Such an arrangement makes it likewise possible to cushion a movement of the cooling element system within the cooling device. Wear of the cooling device due to a contact between the element housing and the device housing is avoided hereby. Furthermore, this reduces the generation of noise within the cooling device. In addition, the especially precise maintenance of a predefined position of the cooling element system within the closed-circuit respirator and, as a result, an especially efficient cooling by the cooling device are made possible. Finally, such an advantageous cooling device without carrying area makes it likewise possible to provide the bead described, which at least partially encloses the common mounting arrangement. All the advantages of this bead in terms of cushioning and flow guidance can therefore likewise be achieved by this advantageous cooling device. Furthermore, all the aforementioned embodiments of the cooling element system, which are not explicitly related to the carrying area, are also advantageous in combination with the device housing as an advantageous cooling device if no carrying area is provided at the collar. Such embodiments of a cooling device that is not according to the present invention, i.e., all combinations of cooling element systems being described here, in which a carrying area with a device housing according to the present invention is abandoned, shall be disclosed hereby as embodiments not according to the present invention.

Furthermore, a closed-circuit respirator with a cooling device according to at least one of the above embodiments is proposed for accomplishing the object according to the present invention.

The closed-circuit respirator according to the present invention is cooled especially efficiently by the cooling device with the cooling element system according to the present invention and can be prepared for a use especially rapidly by the collar with the carrying area. In particular, the number of cooling elements can be inserted and changed especially rapidly and simply. As a result, error-free operation of the cooling device according to the present invention, especially a secure and reliable insertion or replacement of the number of cooling elements, are possible even in the case of a distraction due to events occurring in the surrounding area, as they may typically occur at sites at which a closed-circuit respirator is used.

The present invention shall be explained in greater detail now on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
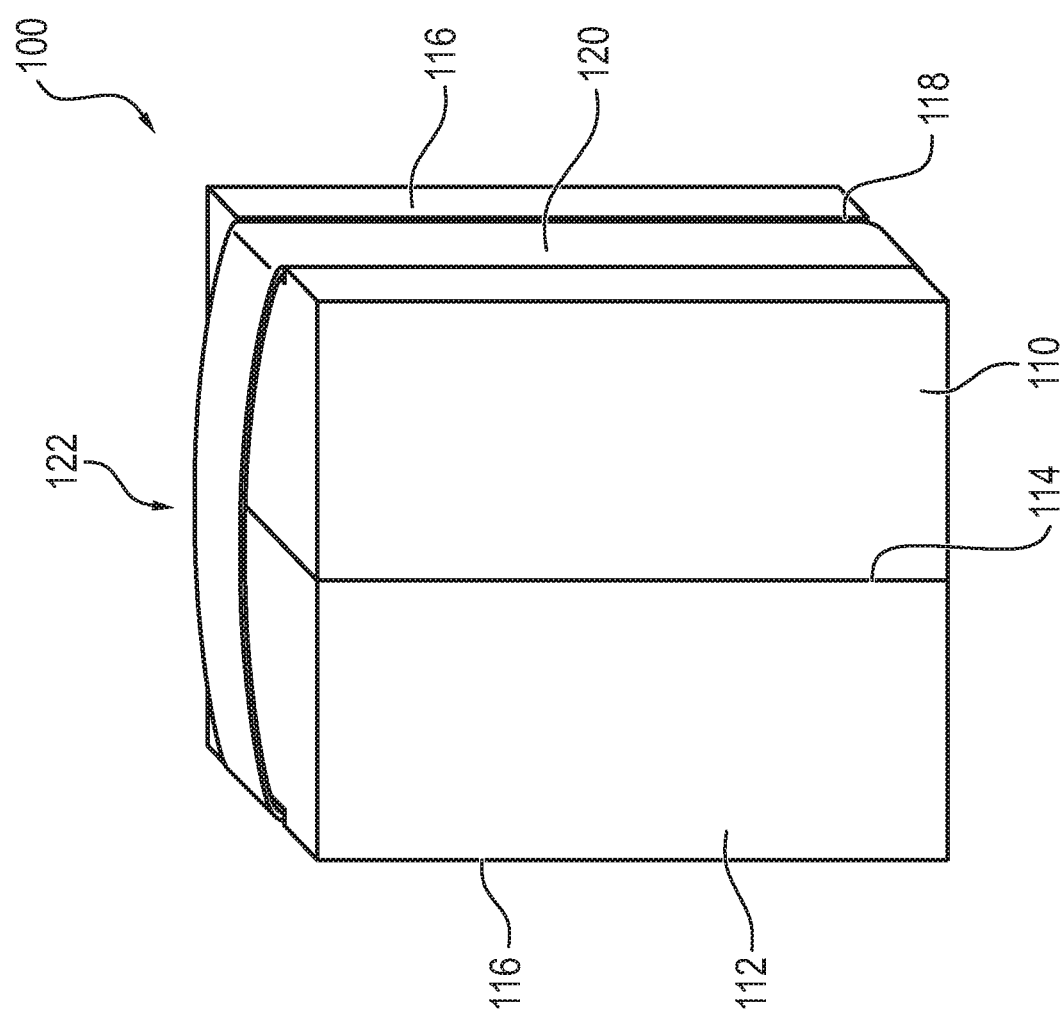
FIG. 1 is a schematic view of a first exemplary embodiment of a cooling element system according to the present invention.

Referring to the drawings, FIG. 1 shows a schematic view of a first exemplary embodiment of a cooling element system 100 according to the present invention.

The cooling element system 100 is intended for use within a cooling device of a closed-circuit respirator. It has a number of cooling elements 110 and a collar 120.

Each cooling element 110 of the number of cooling elements 110 has an element housing 112 each. The element housing 112 is manufactured in this case from a plastic, preferably with the use of an injection molding process. In the exemplary embodiment shown, the number of cooling elements 110 comprise precisely one cooling element. The element housing 112 has a liquid-tight closure, which is a permanent closure in this case, and which is formed by a weld seam 114. Furthermore, the element housing 112 is filled with a coolant (not shown). The element housing 112 allows a mounting arrangement, i.e., a certain orientation in this case, within the cooling device.

The collar 120 encloses the number of cooling elements 110 in the presence of the common mounting arrangement, i.e., for the orientation shown in FIG. 1. The collar 120 has a carrying area 122 here, which is configured to carry the cooling element 110 in the presence of the common mounting arrangement at the carrying area 122. The carrying area 122 is embodied in this case by the collar 120 having a certain distance from the cooling element 110, so that a user can grasp the collar 120 with his hand and can carry as a result the cooling element 110 by means of the collar 120. It is possible hereby to remove the cooling element 110 in the presence of the common mounting arrangement out of the cooling device and to insert it into the cooling device via the carrying area 122.

The collar 120 is formed from a plastic, namely, an elastomer in the exemplary embodiment being shown. As a result, the collar 120 is stretchable and can be placed around the cooling element 110 in a simple manner.

A collar depression 118, by which the collar 120 is held in its position, is provided at the cooling element 110 on at least two opposite lateral surfaces 116 of the cooling element 110 for a reliable contact of the collar 120 with the cooling element 110. The cooling element 110 is cuboid in this case, so that the corresponding lateral areas of the collar 120 are pushed during the carrying of the cooling element system 100 via the carrying area 122 into the respective collar depression 118 and reliable carrying and transportation of the cooling element system are possible as a result. In the exemplary embodiment being shown, the collar 120 is, furthermore, in contact with the base side of the cooling element 110, which side is not shown. In one exemplary embodiment, not shown, the collar is in contact with only exactly two opposite sides of the cooling element, for example, based on an arch of the cooling element on the side located between the two opposite sides. Such an arch prevents a contact of the collar with this side in the exemplary embodiment, which is not shown.

Figure 2:
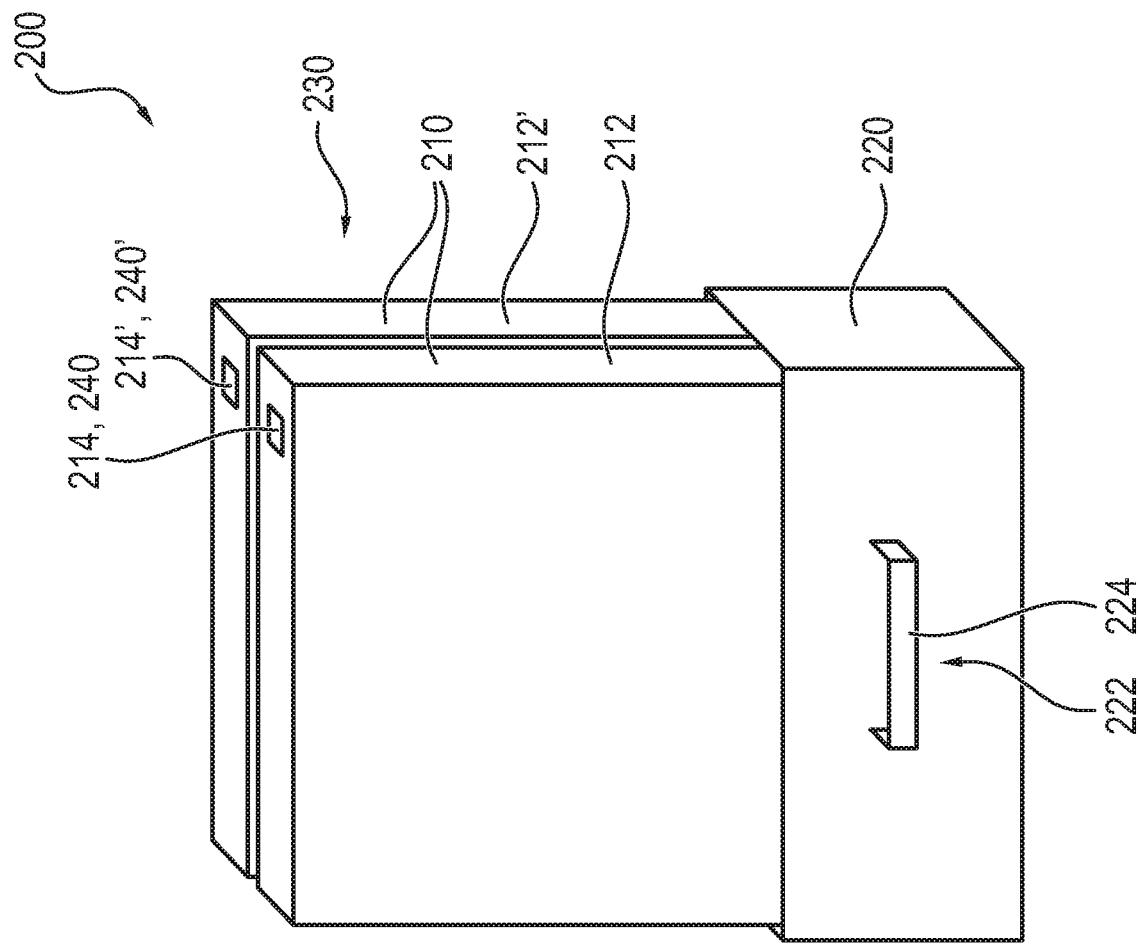
FIG. 2 is a schematic view of a second exemplary embodiment of the cooling element system according to the present invention.

FIG. 2 shows a schematic view of a second exemplary embodiment of the cooling element system according to the present invention.

The cooling element system 200 differs from the cooling element system 100 from FIG. 1 in that the collar 220 is rigid and is not formed from an elastomer. The collar 220 encloses here a bottom area of the shown common mounting arrangement of the number of cooling elements 210. The carrying area 222 of the collar 220 is formed by a rigid grip 224. The collar 220 is in contact in the exemplary embodiment shown on five sides of the common mounting arrangement, namely, on all sides except the upwardly pointing side.

The number of cooling elements 210 comprise here two cooling elements 210, whose element housings 212, 212' have a plate shape configuration. The shown common mounting arrangement of the number of cooling elements 210 comprises a layering of the two plate shape element housings 212, 212' into a stack of plates 230.

The respective liquid-tight closure 214, 214' of the respective cooling element 210 is a detachable screw cap, which is protected by the respective cover 240, 240' shown in FIG. 2 from environmental effects.

Due to the arrangement of the collar 220, it is especially advantageously possible to pull the cooling element system 200 out of a compartment of the corresponding cooling device, which compartment is provided for that purpose, for changing or removing the cooling elements. In the exemplary embodiment shown, the cooling elements 210 of the number of cooling elements are connected via an elastic mount within the collar 220 to the collar 220 in a non-positive manner. In one exemplary embodiment, not shown, at least one cooling element of the cooling element system is detachably connected to the collar via a positive-locking mechanism, especially via a locking mechanism.

Figure 3:
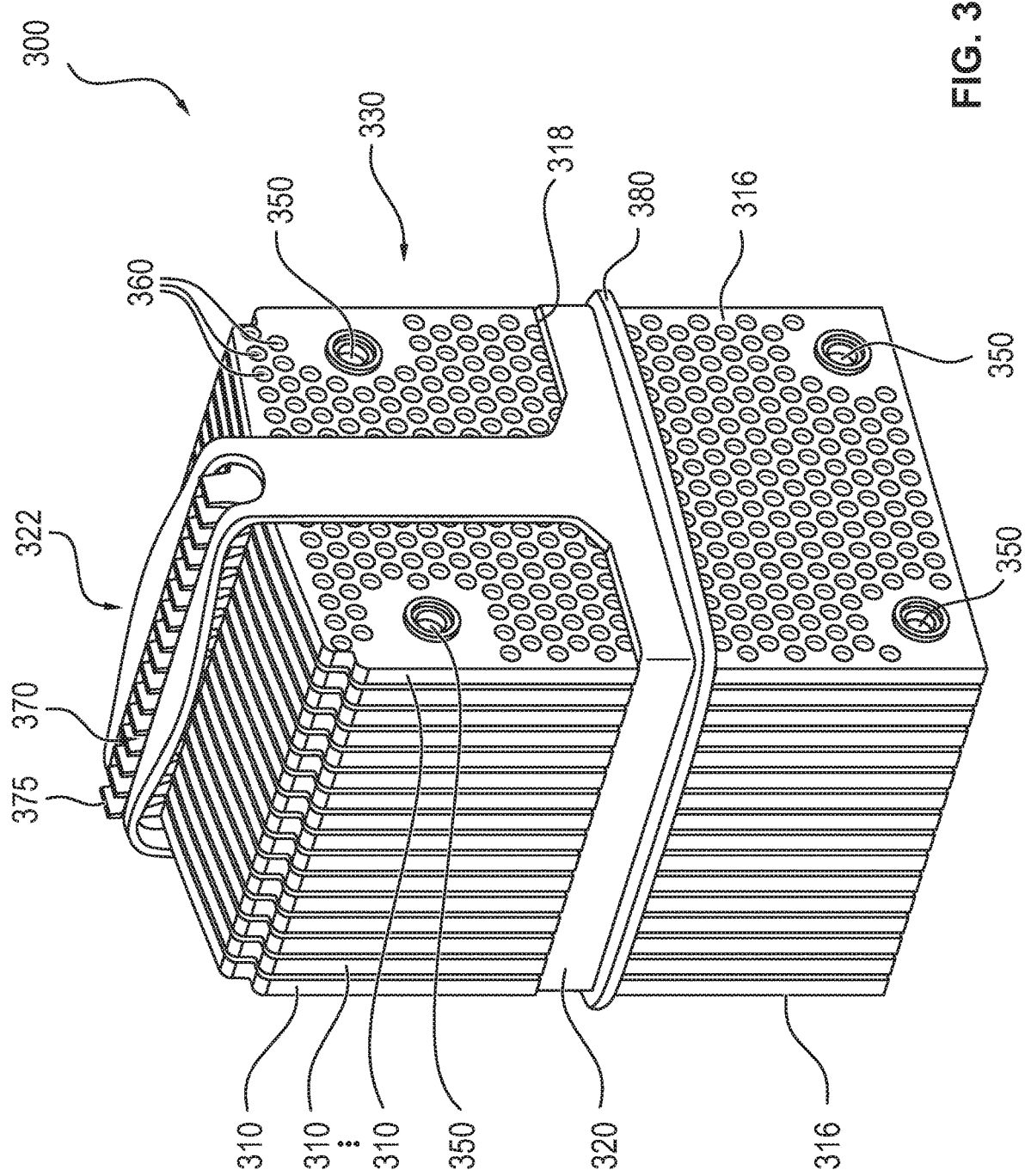
FIG. 3 is a schematic view of a third exemplary embodiment of the cooling element system according to the present invention.

FIG. 3 shows a schematic view of an especially advantageous, third exemplary embodiment of the cooling element system 300 according to the present invention.

The number of cooling elements 310 have individual cooling elements 310, which have a plate shape configuration each. The shown common mounting arrangement of the number of cooling elements 310 comprises a layering of the plate shape cooling elements 310 into a stack of plates 330.

Four depressions 350 are shown on the outer surface of the cooling element 310 in the frontmost position. Corresponding elevations, which are arranged on the outer surface of this cooling element 310, which outer surface is located opposite thereto, are not shown. Each of the 16 cooling elements 310 of the number of cooling elements 310 correspondingly comprises these four depressions 350 and the corresponding elevations, not shown, wherein the respective elevations mesh with a respective depression 350 of the adjacent cooling element 310 of the stack of plates 330.

Furthermore, a plurality of arches 360 are shown on the outer surface of the cooling element 310 shown in the frontmost position. Such arches 360 are provided on all outer surfaces of the cooling elements 310. As a result, a heat exchange between cooling elements and breathing gas flowing through is especially efficient, because a comparatively large surface is available in view to the volume of the cooling element for this heat exchange and for the cooling of the breathing gas, which takes place as a result.

The collar 320 is formed from an elastomer and is in contact on four adjacent sides of the stack of plates 330 in a non-positive manner. The collar has a carrying area 322 here, which extends from a section of the collar 320 on one side of the stack of plates 330 over a top side of the stack of plates 330 to a section of the collar 320 on the opposite side of the stack of plates 330. The elastic carrying area 322 of the collar 320 has a flow guide opening 370 in the area of the top side of the stack of plates 330. This flow guide opening 370 makes place for a respective projection 375 of a respective cooling element 310 and makes, furthermore, possible a flow of the breathing gas through the flow guide opening 370.

In the especially advantageous exemplary embodiment shown, the number of cooling elements 310 can be held by the collar 320 especially securely and reliably. A collar depression 318 is thus provided on two opposite lateral surfaces 316 of a respective cooling element 310 of the number of cooling elements 310. As a result, the collar 320 can be in contact especially reliably with the common mounting arrangement of the number of cooling elements 310, which said mounting arrangement is formed as a stack of plates 330. Further, the cooling elements 310 are pressed by the elastic collar especially reliably against one another and held thereby in their common mounting arrangement. In particular, the combination of the collar depression 318 present here and the respective elevations and depressions 350 on each cooling element 310 ensure that the individual cooling elements cannot slip relative to one another within the stack of plates 330, so that the number of cooling elements 310 are held securely by the collar 320 in their common mounting arrangement. In addition, the flow guide opening 370 at the carrying area 322 additionally ensures by means of the projections 375 located in between that individual plate shape cooling elements cannot twist or be displaced relative to one another.

Furthermore, the collar 320 has a bead 380 at its area extending around the four adjacent sides of the stack of plates 330. This bead 380 extends here around the entire mounting arrangement, i.e., the entire stack 330. In one exemplary embodiment, not shown, the bead extends only partially around the common mounting arrangement. In another exemplary embodiment, not shown, a plurality of beads are provided at the collar. In the exemplary embodiment shown, the bead 380 allows an impact protection and/or a cushioning for the cooling element system 300 if it moves within the corresponding cooling device relative to the cooling device. As a result, a wear or a damage to components of the correspondingly configured closed-circuit respirator can be avoided. Furthermore, generation of noise within the closed-circuit respirator can be avoided.

In one example, which is not according to the present invention, the collar is configured without a carrying area but otherwise as shown in FIG. 3. Such a collar has, furthermore, the advantage that it holds the cooling elements of the cooling device securely together and protects the cooling element system as an impact protection and/or as a cushioning against a contact with the rest of the cooling device. Such a collar, which is not according to the present invention, may be used in an especially advantageous combination with a number of cooling elements that have a plate shape configuration and cause, due to corresponding depressions and elevations, the cooling elements to be able to mesh with one another and correspondingly not to be displaced against one another. In view to the impact protection associated therewith and the possible, especially precise positioning of the cooling elements, all exemplary embodiments shown are also advantageous if the corresponding collar has no carrying area.

The collar 330 has a thickness of at least 2 mm, especially at least 5 mm in the areas outside the bead 380, and the bead 380 has a thickness of at least 0.5 mm, especially at least 0.8 mm and especially preferably at least 1.0 cm.

The collar depression 318 has a depth that is greater than the thickness of the collar 330 in the areas outside the bead 380 and that is flatter than the thickness of the bead 380. It is ensured hereby that the collar 320 can exert via the bead 380 a cushioning effect during a movement within the cooling device.

Figure 4:
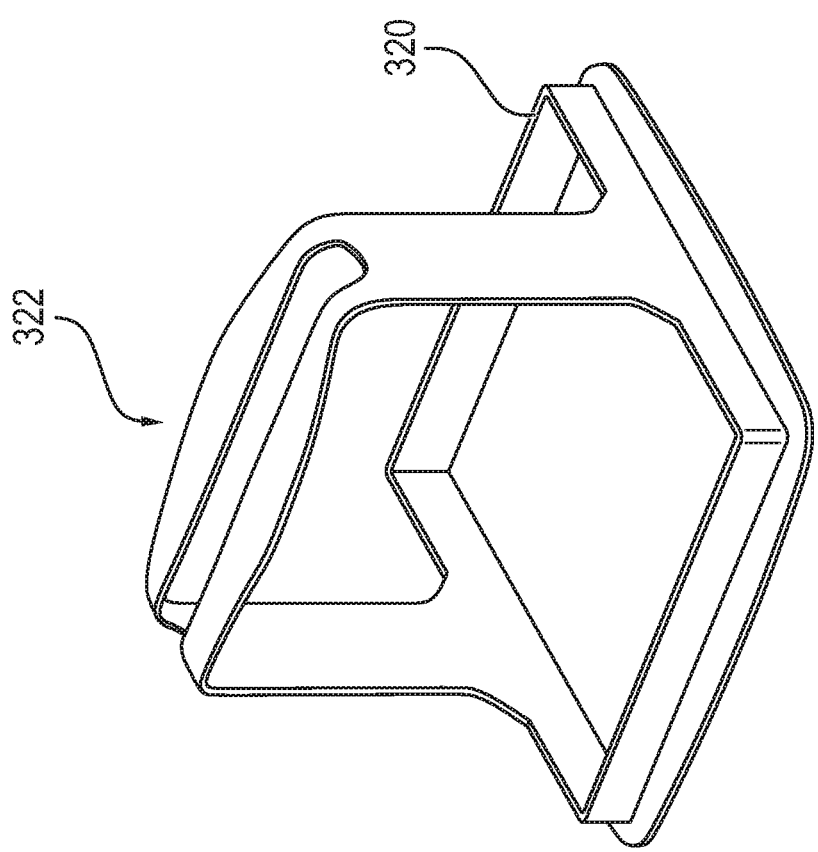
FIG. 4 is a schematic view of the collar from the third exemplary embodiment of the cooling element system according to the present invention.

FIG. 4 shows a schematic view of the collar 320 from the third exemplary embodiment of the cooling element system 300 according to the present invention.

In addition to the view of the collar 320 from FIG. 3, FIG. 4 shows that the collar has a symmetrical configuration and provides as a result a uniform pulling force for carrying the stack of plates 330 via the collar depression 318. In the exemplary embodiment shown, the carrying area 322 has a lateral extension that equals at least 7 cm, especially at least 10 cm and especially preferably at least 15 cm. The cooling element system 300 can be carried as a result especially comfortably by a user via the carrying area 322, because this lateral extension approximately corresponds to the width of a hand.

The collar 320 has a one-part configuration in the exemplary embodiment shown. Furthermore, the collar 320 is manufactured by an injection molding process.

Figure 5:
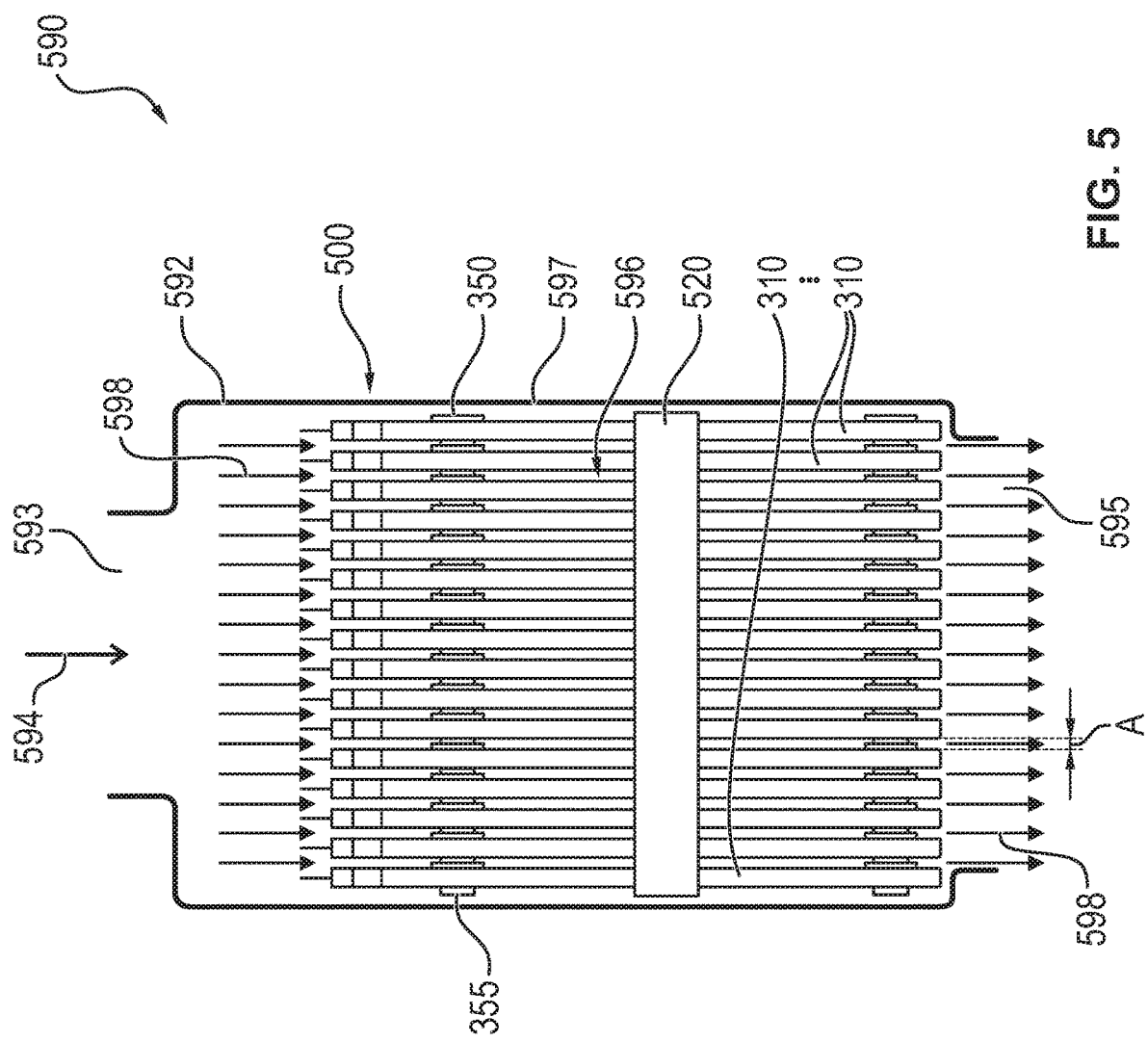
FIG. 5 is a schematic view of a first exemplary embodiment of a cooling device according to the present invention.

FIG. 5 shows a schematic view of a first exemplary embodiment of a cooling device 500 according to the present invention.

The cooling device 590 comprises the cooling element system 500 and a device housing 592.

The cooling element system 500 differs from the cooling element system 300 shown in FIG. 3 only in that the collar 520 has no bead 380. The cooling elements 310 and the collar 520 otherwise have exactly the same configuration as in the cooling element system 300.

The device housing 592 has a gas inlet 593, which is configured to bring a gas 594 to be cooled into the device housing 592. Further, the device housing 592 has a gas outlet 595, which is configured to let the gas admitted into the device housing 592 out of the device housing 592. Further, the device housing 592 has a device volume 596, which is enclosed by a housing wall 597 of the device housing 592 and which can replaceably accommodate the cooling element system 500. The device housing 592 is configured here to carry the gas stream 598 of the gas 594 to be cooled from the gas inlet 593 through the cooling element system 500 arranged in the device volume 596 to the gas outlet 595.

The depressions 350 and elevations 355 at the cooling elements 310 cause, as is shown in FIG. 5, a distance A, which allows the gas stream 598 between the individual cooling elements 310, to be maintained between the cooling elements 310. As a result, the cooling of the gas 594 to be cooled is possible in an efficient manner, because an especially large outer surface of the cooling elements is available for the heat exchange between cooling elements 310 and gas 594 to be cooled.

The distance A between the cooling elements 310 equals here at least 2.0 mm, especially at least 3.0 mm and preferably at least 5.0 mm.

FIG. 5 additionally shows that the elastic collar 520 protects the cooling element system 500 from damage by shocks between cooling elements and housing wall 597.

Figure 6:
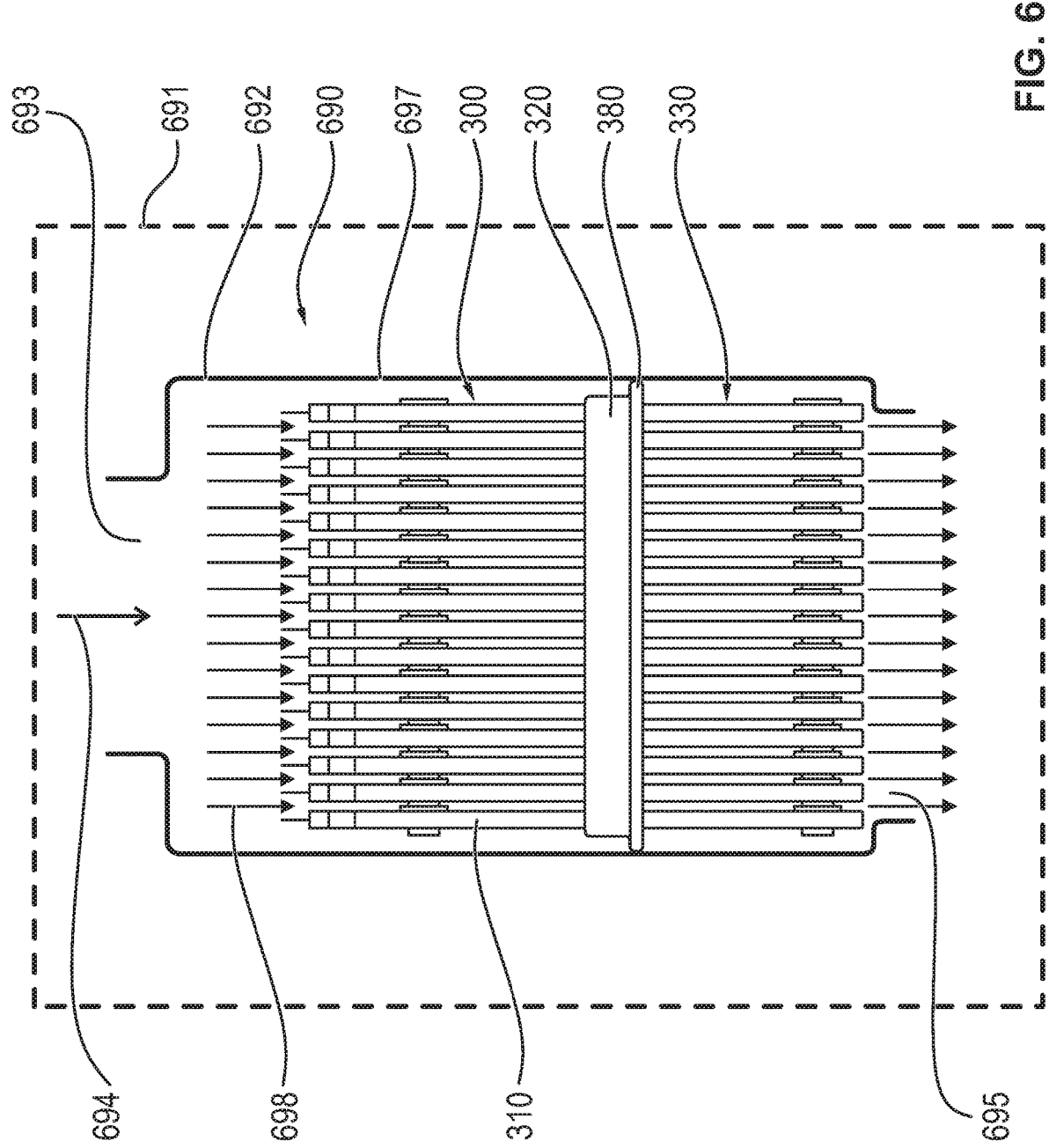
FIG. 6 is a schematic view of a closed-circuit respirator with a schematic view of a second exemplary embodiment of the cooling device according to the present invention with the cooling device within a closed-circuit respirator according to the present invention.

FIG. 6 shows a schematic view of a second exemplary embodiment of the cooling device 690 according to the present invention within a closed-circuit respirator 691 according to the present invention.

Contrary to the cooling device 590 shown in FIG. 5, the cooling device 690 has precisely the cooling element system 300 shown in FIG. 3. Consequently, the collar 320 of the cooling device 590 has the bead 380.

The device housing 692 is configured such that the housing wall 697 is touched by the bead 380, so that the bead 380 closes the area between the stack of plates 330 and the housing wall 697 at least in an essentially airtight manner. Based on the elastic properties of the collar 320, it is possible to insert the cooling element system 300 into the device housing 692 by a simple pushing in. To insert or remove the cooling element system 300 from the cooling device 690, a flap is opened in the area of the gas inlet 693 (not shown).

The bead 380 reduces the gas stream 698 of the gas to be cooled such that the gas stream 698 cannot reach the gas outlet 695 directly passing by the cooling elements 310 without being cooled by the cooling elements 310. The gas stream 698 is sent therefore through the areas between the cooling elements 310 due to a blocking of the gas by the bead 380.

In one exemplary embodiment, not shown, at least one ventilation line opening, through which an air stream is possible in the edge area of the device volume, which edge area is otherwise sealed by the bead, is provided in the collar. The air stream flowing through the cooling device is made uniform by this air stream in this exemplary embodiment. The size of the at least one ventilation line opening is selected especially preferably to be such that such a volume flow of the gas flowing through is possible through all ventilation line openings as through a gap formed between two cooling elements. An especially uniform air stream is possible through the cooling device in this especially preferred exemplary embodiment, which is not shown.

The basic guiding of the breathing gas within the closed-circuit respirator 691 is known. In particular, arrangement of the cooling device 690 directly in front of an outlet of the closed-circuit respirator 691 is known, so that a user of the closed-circuit respirator 691 can use the breathing air cooled by the cooling device 690 almost immediately.

While specific embodiments of the invention have been shown and described in detail to illustrate the application of the principles of the invention, it will be understood that the invention may be embodied otherwise without departing from such principles.

LIST OF REFERENCE CHARACTERS 100, 200, 300, 500 Cooling element system
110, 210, 310 Cooling element
112, 212, 212' Element housing
114, 214, 214' Liquid-tight closure
116, 316 Opposite lateral surfaces
118, 318 Collar depression
120, 220, 320, 520 Collar
122, 222, 322 Grip area
224 Rigid grip
230, 330 Stack of plates
240, 240' Cover
350 Depression
355 Elevation
360 Arches
370 Flow guide openings
375 Projection
380 Bead
590, 690 Cooling device
592, 692 Device housing
593, 693 Gas inlet
594, 694 Gas to be cooled
595, 695 Gas outlet
596 Device volume
597, 697 Housing wall
598, 698 Gas stream
691 Closed-circuit respirator
A Distance

What is claimed is:

1. A cooling element system for use within a cooling device of a closed-circuit respirator, the cooling element system comprising:

a plurality of cooling elements, each of the plurality of cooling elements comprising an element housing, which has a liquid-tight closure and is filled with a coolant or fillable with a coolant, wherein the element housings are connected to provide a common mounting arrangement of the plurality of cooling elements within the cooling device; and a collar enclosing the plurality of cooling elements in the common mounting arrangement, the collar having a carrying area configured to allow for carrying of the plurality of cooling elements in the common mounting arrangement via the carrying area, whereby one or more of the plurality of cooling elements in the common mounting arrangement is removable from the cooling device via the carrying area and one or more of the plurality of cooling elements in the common mounting arrangement is insertable into the cooling device via the carrying area, the collar being configured to press one of the plurality of cooling elements in a direction of another one of the plurality of cooling elements and to press the another one of the plurality of cooling elements in a direction of the one of the plurality of cooling elements.

2. The cooling element system in accordance with claim 1, wherein the collar is formed from a plastic.

3. The cooling element system in accordance with claim 2, wherein the collar is formed from an elastomer.

4. The cooling element system in accordance with claim 1, wherein the element housings of the plurality of cooling elements have a plate shape configuration.

5. The cooling element system in accordance with claim 4, wherein the common mounting arrangement of the plurality of cooling elements comprises a layering of the plate shape element housings to provide a stack of plates.

6. The cooling element system in accordance with claim 5, wherein:
each plate shape configuration has an elevation and a corresponding depression;
a respective elevation of an element housing meshes within a depression of another element housing of the stack of plates.

7. The cooling element system in accordance with claim 5, wherein the collar is in contact with at least two opposite sides of the stack of plates of the plurality of cooling elements.

8. The cooling element system in accordance with claim 1, wherein the element housings of the plurality of cooling elements are shaped such that in the common mounting arrangement a collar depression encloses the common mounting arrangement at least partially and is configured to allow a contact of the collar with the element housings.

9. The cooling element system in accordance with claim 1, wherein the collar has at least one flow guide opening.

10. A cooling device for a closed-circuit respirator, the cooling device comprising:
a cooling element system comprising:
a plurality of cooling elements, each of the plurality of cooling elements comprising an element housing, which has a liquid-tight closure and is filled with a coolant or fillable with a coolant, wherein the element housings cooperate to provide a common mounting arrangement of the plurality of cooling elements within the cooling device; and
a collar enclosing the plurality of cooling elements in the common mounting arrangement, the collar having a carrying area configured to allow for carrying of the plurality of cooling elements in the common mounting arrangement via the carrying area, whereby one or more of the plurality of cooling elements in the common mounting arrangement is removable from the cooling device via the carrying area and one or more of the plurality of cooling elements in the common mounting arrangement is insertable into the cooling device via the carrying area, the collar being configured to press one of the plurality of cooling elements in a direction of another one of the plurality of cooling elements and to press the another one of the plurality of cooling elements in a direction of the one of the plurality of cooling elements;
a device housing with a gas inlet configured to admit a gas to be cooled into the device housing and a gas outlet configured to release admitted gas that has been cooled out of the device housing and with a device volume, which is enclosed by a housing wall of the device housing, the device volume replaceably accommodating the cooling element system, wherein the device housing is configured such that a gas stream of the gas to be cooled flows from the gas inlet through the cooling element system arranged in the device volume to the gas outlet.

11. The cooling device in accordance with claim 10, wherein the collar is configured to enclose the common mounting arrangement of the plurality of cooling elements such that a bead of the collar, which bead points away from the plurality of cooling elements and at least partially encloses the common mounting arrangement, is in contact with the housing wall of the device housing in an inserted state of the cooling element system and thereby reduces an area through which the gas stream of the gas to be cooled is able to flow.

12. A closed-circuit respirator comprising a cooling device, the cooling device comprising:
a cooling element system comprising:
a plurality of cooling elements, each of the plurality of cooling elements comprising an element housing, which has a liquid-tight closure and is filled with a coolant or fillable with a coolant, wherein the element housings cooperate to provide a common mounting arrangement of the plurality of cooling elements within the cooling device; and
a collar enclosing the plurality of cooling elements in the common mounting arrangement, the collar having a carrying area configured to allow for carrying of the plurality of cooling elements in the common mounting arrangement via the carrying area, whereby one or more of the plurality of cooling elements in the common mounting arrangement is removable from the cooling device via the carrying area and one or more of the plurality of cooling elements in the common mounting arrangement is insertable into the cooling device via the carrying area, the collar being configured to press one of the plurality of cooling elements in a direction of another one of the plurality of cooling elements and to press the another one of the plurality of cooling elements in a direction of the one of the plurality of cooling elements;
a device housing with a gas inlet configured to admit a gas to be cooled into the device housing and a gas outlet configured to release admitted gas to be cooled out of the device housing and with a device volume, which is enclosed by a housing wall of the device housing, the device volume replaceably accommodating the cooling element system, wherein the device housing is configured such that a gas stream of the gas to be cooled flows from the gas inlet through the cooling element system arranged in the device volume to the gas outlet.

13. The closed-circuit respirator in accordance with claim 12, wherein the element housing of each of the plurality of cooling elements comprises a surface extending in a longitudinal direction of the element housing, the surface of the element housing of the one of the plurality of cooling elements and the surface of the element housing of the another one of the plurality of cooling elements defining a fluid flow channel for receiving a flow of fluid.

14. The closed-circuit respirator in accordance with claim 12, wherein the common mounting arrangement comprises a first side, a second side, a third side, a fourth side and a fifth side, the first side being perpendicular to the second side, the second side being perpendicular to the third side, the third side being perpendicular to the fourth side, the fifth side being perpendicular to the first side, the second side, the third side and the fourth side, the collar extending about the first side, the second side, the third side and the fourth side, the carrying area being located opposite the fifth side.

15. The closed-circuit respirator in accordance with claim 12, wherein the element housing of the one of the plurality of cooling elements and the element housing of the another one of the plurality of cooling elements define a fluid flow channel for receiving a flow of fluid, the flow channel being parallel to a longitudinal direction of the cooling elements.

16. The cooling device in accordance with claim 10, wherein the element housing of each of the plurality of cooling elements comprises a surface extending in a longitudinal direction of the element housing, the surface of the element housing of the one of the plurality of cooling elements and the surface of the element housing of the another one of the plurality of cooling elements defining a flow channel for receiving a flow of fluid.

17. The cooling device in accordance with claim 10, wherein the common mounting arrangement comprises a first side, a second side, a third side, a fourth side and a fifth side, the first side being perpendicular to the second side, the second side being perpendicular to the third side, the third side being perpendicular to the fourth side, the fifth side being perpendicular to the first side, the second side, the third side and the fourth side, the collar extending about the first side, the second side, the third side and the fourth side, the carrying area being located opposite the fifth side.

18. The cooling device in accordance with claim 10, wherein the element housing of the one of the plurality of cooling elements and the element housing of the another one of the plurality of cooling elements define a flow channel for receiving a flow of fluid, the flow channel being parallel to a longitudinal direction of the cooling elements.

19. The cooling element system in accordance with claim 1, wherein the element housing of the one of the plurality of cooling elements and the element housing of the another one of the plurality of cooling elements define a fluid flow channel for receiving a flow of fluid, the flow channel being parallel to a longitudinal direction of the cooling elements.

20. The cooling element system in accordance with claim 19, wherein the collar is configured to apply a force to the one of the plurality of cooling elements and to the another one of the plurality of cooling elements, the force being perpendicular to the fluid flow channel.

* * * * *